(12) United States Patent
Shah

(10) Patent No.: US 8,585,676 B2
(45) Date of Patent: Nov. 19, 2013

(54) MULTI-LUMEN LAY-FLAT TUBING, CATHETER ARTICLES COMPRISING SAME, AND METHOD OF MANUFACTURE THEREOF

(75) Inventor: Tilak M. Shah, Cary, NC (US)

(73) Assignee: Polyzen Inc., Apex, NC (US)

( * ) Notice: Subject to any disclaimer, the term of this patent is extended or adjusted under 35 U.S.C. 154(b) by 461 days.

(21) Appl. No.: 12/026,297

(22) Filed: Feb. 5, 2008

(65) Prior Publication Data

US 2008/0188802 A1    Aug. 7, 2008

Related U.S. Application Data

(60) Provisional application No. 60/888,297, filed on Feb. 5, 2007.

(51) Int. Cl.
*A61M 31/00* (2006.01)
(52) U.S. Cl.
USPC ........................................................ 604/506
(58) Field of Classification Search
USPC ............ 604/96.01–103.14, 164.01, 264, 508, 604/509, 523, 544, 103, 912, 915; 600/433–435, 466, 585, 115, 116; 607/122; 623/23.52, 8; 606/191–195; 264/491

See application file for complete search history.

(56) References Cited

U.S. PATENT DOCUMENTS

| 4,043,345 A | * | 8/1977 | Kramann et al. ............. 604/271 |
| 4,311,146 A | | 1/1982 | Wonder |
| 4,464,175 A | | 8/1984 | Altman et al. |
| 4,650,463 A | * | 3/1987 | LeVeen et al. ................ 604/43 |
| 4,784,133 A | * | 11/1988 | Mackin ............................ 606/7 |
| 5,116,310 A | * | 5/1992 | Seder et al. .................... 604/43 |
| 5,219,792 A | * | 6/1993 | Kim et al. ..................... 438/631 |
| 5,234,454 A | | 8/1993 | Bangs |

(Continued)

OTHER PUBLICATIONS

Co-Pending U.S. Appl. No. 12/106,743, entitled "Ostomy Bag Mounting Structure", filed Apr. 21, 2008 in the name of Tilak Shah.

(Continued)

*Primary Examiner* — Nicholas Lucchesi
*Assistant Examiner* — Scott Medway
(74) *Attorney, Agent, or Firm* — Hultquist, PLLC; Steven J. Hultquist

(57) ABSTRACT

A multi-lumen lay-flat tube formed of polymeric film material, e.g., polyurethane elastomer film, comprising a main tube and at least one interior tubular passage, wherein each of the at least one interior tubular passage is constituted by reentrant portions of polymeric film material forming the main tube. The multi-lumen lay-flat tube can be utilized for fabrication of a balloon catheter, or other indwelling catheter device. The multi-lumen lay-flat tube can be formed by a fabrication method including provision of superposed sheets of polymeric film material, welding the superposed sheets of polymeric film material along generally parallel, spaced-apart seam lines to form at least two passages bounded by a successive pair of such seam lines, and if desired everting the welded superposed sheets to form a main tube having at least one tubular passage therewithin. In another implementation, a multi-lumen lay-flat tube can be formed by bonding concentric tubes to one another along longitudinally extending seals, and in a still further implementation, a multi-lumen lay-flat tube can be formed by bonding a strip member longitudinally along a tube, with the strip member being bonded at its margins to the tube, to enclose a passage between the strip member and the tube.

14 Claims, 5 Drawing Sheets

(56) References Cited

U.S. PATENT DOCUMENTS

| | | | |
|---|---|---|---|
| 5,360,414 A * | 11/1994 | Yarger | 604/264 |
| 5,433,252 A * | 7/1995 | Wolf et al. | 138/113 |
| 5,527,280 A | 6/1996 | Goelz | |
| 5,679,423 A | 10/1997 | Shah | |
| 5,807,333 A | 9/1998 | Osborne et al. | |
| 5,833,915 A | 11/1998 | Shah | |
| 5,879,499 A * | 3/1999 | Corvi | 156/175 |
| 5,924,456 A * | 7/1999 | Simon | 138/122 |
| 5,951,514 A * | 9/1999 | Sahota | 604/101.05 |
| 5,996,639 A * | 12/1999 | Gans et al. | 138/115 |
| 6,022,313 A * | 2/2000 | Ginn et al. | 600/114 |
| 6,249,708 B1 * | 6/2001 | Nelson et al. | 607/122 |
| 6,270,477 B1 | 8/2001 | Bagaoisan et al. | |
| 6,291,543 B1 | 9/2001 | Shah | |
| 6,352,077 B1 | 3/2002 | Shah | |
| 6,460,541 B1 | 10/2002 | Shah et al. | |
| 6,478,789 B1 * | 11/2002 | Spehalski et al. | 604/540 |
| 6,592,544 B1 * | 7/2003 | Mooney et al. | 604/43 |
| 6,663,646 B1 | 12/2003 | Shah | |
| 6,712,832 B2 | 3/2004 | Shah | |
| 6,805,662 B2 | 10/2004 | Shah et al. | |
| 6,827,710 B1 * | 12/2004 | Mooney et al. | 604/500 |
| 6,875,193 B1 * | 4/2005 | Weisel et al. | 604/22 |
| 6,960,199 B2 | 11/2005 | Burkett et al. | |
| 7,112,186 B2 | 9/2006 | Shah | |
| 7,220,252 B2 | 5/2007 | Shah | |
| 2003/0088209 A1 * | 5/2003 | Chiu et al. | 604/96.01 |
| 2005/0222329 A1 | 10/2005 | Shah | |
| 2006/0129094 A1 | 6/2006 | Shah | |
| 2006/0212064 A1 | 9/2006 | Shah | |
| 2007/0212559 A1 | 9/2007 | Shah | |
| 2007/0239110 A1 | 10/2007 | Shah | |
| 2007/0299463 A1 | 12/2007 | Shah | |
| 2009/0082724 A1 | 3/2009 | Shah et al. | |

OTHER PUBLICATIONS

Co-Pending U.S. Appl. No. 12/106,760, entitled, "Extrusion Blow-Molded Corporeal Port Mounting Structure", filed Apr. 21, 2008 in the name of Tilak Shah.

* cited by examiner

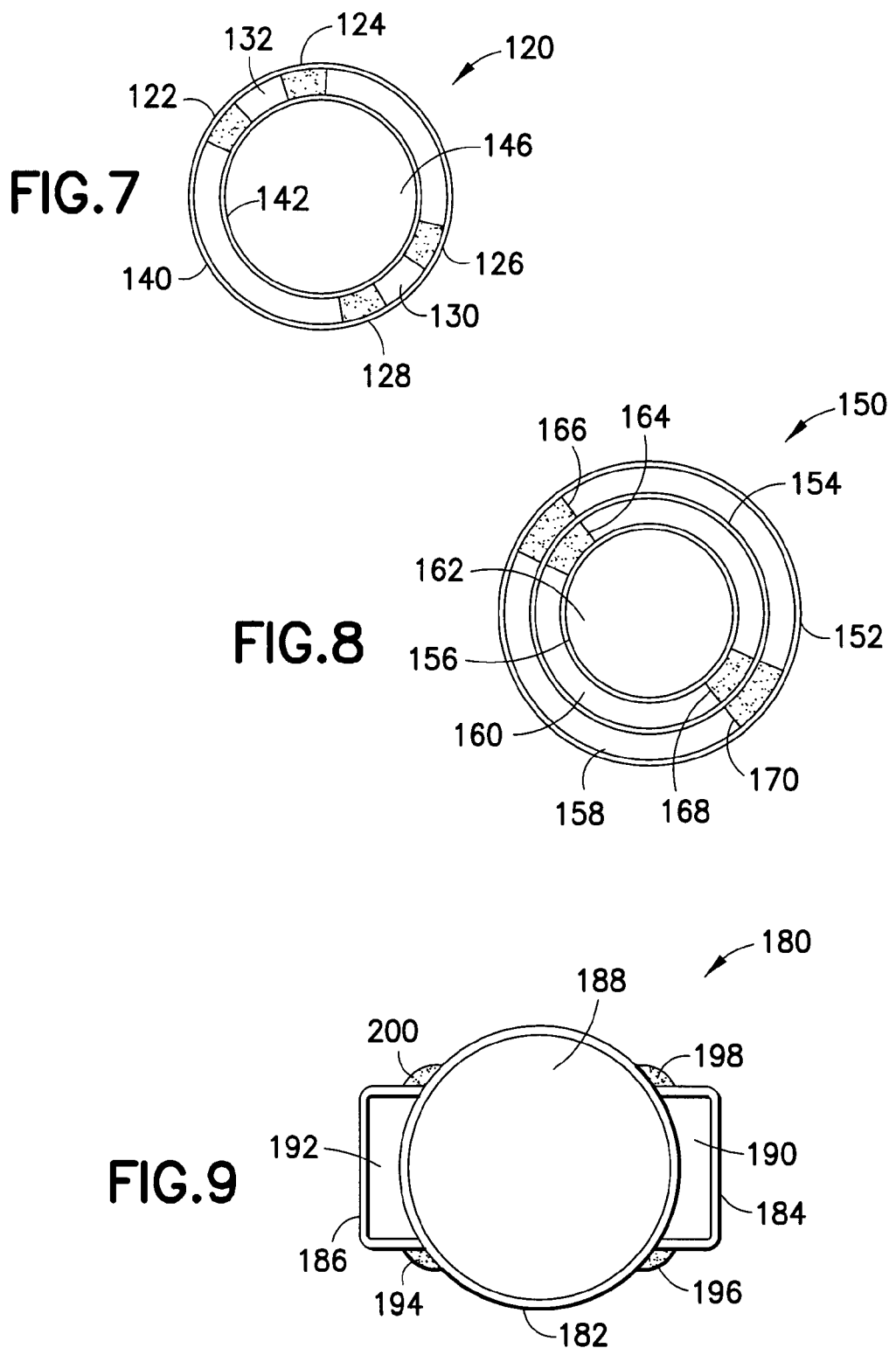

MULTI-LUMEN LAY-FLAT TUBING, CATHETER ARTICLES COMPRISING SAME, AND METHOD OF MANUFACTURE THEREOF

CROSS-REFERENCE TO RELATED APPLICATIONS

This application claims the benefit of U.S. Provisional Patent Application No. 60/60/888,297 filed Feb. 5, 2007 in the name of Tilak M. Shah. The disclosure of such application is hereby incorporated herein by reference in its entirety.

FIELD OF THE INVENTION

The present invention relates to multi-lumen lay-flat tubing, to catheter articles comprising same, such as indwelling balloon catheters, and to methods of making same.

DESCRIPTION OF THE RELATED ART

Single and multi-lumen catheters are widely used in the treatment of a variety of disease states and physiological conditions, and in the course of medical intervention. Such catheters are conventionally formed by common techniques known in the art, most typically tubing extrusion processes. In some cases such catheters are formed by dip coating processes, in which resin solution is coated on a mandrel to build up a desired wall thickness of tubing, and later the mandrel is removed.

In general, dip coating processes for the manufacture of catheter articles are expensive, particularly when the catheter is of a multi-lumen character.

Neither of the extrusion or dip coating approaches employed in the prior art is satisfactory for production of a multi-lumen large diameter tubing with a very thin wall, as required for certain indwelling catheter devices used in the gastrointestinal tract.

In consequence, the art continues to seek improvements in thin wall, large diameter multi-lumen catheter design and fabrication.

SUMMARY OF THE INVENTION

The present invention relates to multi-lumen lay-flat tubing catheters and methods of making the same, as well as to articles comprising such multi-lumen catheters.

In one aspect, the invention relates to a multi-lumen lay-flat tube formed of polymeric film material, comprising a main tube and at least one interior tubular passage, wherein each of the at least one interior tubular passage is constituted by reentrant portions of polymeric film material forming the main tube.

In another aspect, the invention relates to a multi-lumen lay-flat tubing formed of polymeric film material, comprising a tube-within-a-tube or multiple tubes-within-a-tube conformation, with film layers being longitudinally welded at multiple locations to create desired multiple lumens.

In yet another aspect, the invention relates to a multi-lumen lay-flat tubing formed by providing a single lumen lay-flat tubing and welding one or more long strip(s) of film longitudinally to create one or more longitudinal passage(s) to create a multi-lumen tubing structure.

In another aspect, the invention relates to a balloon catheter, comprising:
a multi-lumen lay-flat tube formed of polymeric film material, comprising a main tube and at least one interior tubular passage which may for example be formed as above described; and an inflatable balloon secured to one end of the main tube, with one of said at least one interior tubular passage being in fluid communication with an interior volume of the inflatable balloon.

In another specific aspect, the invention relates to a balloon catheter, comprising:
a multi-lumen lay-flat tube formed of polymeric film material, comprising a main tube and at least one interior tubular passage, wherein each of the at least one interior tubular passage is constituted by reentrant portions of polymeric film material forming the main tube; and an inflatable balloon secured to one end of the main tube, with one of said at least one interior tubular passage being in fluid communication with an interior volume of the inflatable balloon.

In a further aspect, the invention relates to a method of forming a multi-lumen lay-flat tube, comprising:
   providing superposed sheets of polymeric film material;
   welding said superposed sheets of polymeric film material along generally parallel, spaced-apart seam lines to form at least two passages bounded by a successive pair of said seam lines; and
   everting said welded superposed sheets to form a main tube having at least one tubular passage therewithin.

The invention in one aspect provides a method of making a multi-lumen lay-flat tubing article, involving providing concentric first and second tube members, and heat sealing the first and second to members to one another at circumferentially spaced-apart locations extending lengthwise along the tube members, to form a passage bounded by the circumferentially spaced-apart heat seals and interior facing wall portions of the tube members between such heat seals.

A further aspect of the invention relates to a method of making a multi-lumen lay-flat tubing article, by providing concentric first and second tube members, and sealing the first and second to members to one another at circumferentially spaced-apart locations extending lengthwise along the tube members, to form a passage bounded by the circumferentially spaced-apart seals and interior facing wall portions of the tube members between such seals.

A still further aspect of the invention relates to a method of making a multi-lumen lay-flat tube, comprising providing a first tube member, and adhesively bonding margins of an elongate strip to a surface of the first tube member, to form a longitudinally extending passage bounded by facing surfaces of the elongate strip and first tube member and adhesively bonded margins of the elongate strip.

In another aspect, the invention relates to a multi-lumen lay-flat tube, comprising concentric tube members, bonded to one another at longitudinally extending, circumferentially spaced-apart seals, to form at least one passage bounded by facing surfaces of the tube members and the circumferentially spaced-apart seals.

A further aspect of the invention relates to a multi-lumen lay-flat tube, comprising a tube member having bonded thereto a strip member longitudinally extending along the tube member, with the strip member bonded at margins thereof to the tube member to form an enclosed passage between the strip member and tube member.

Other aspects, features and embodiments of the invention will be more fully apparent from the ensuing disclosure and appended claims.

BRIEF DESCRIPTION OF THE DRAWINGS

FIG. 7 is a cross-sectional view of a multi-lumen catheter, according to another embodiment of the invention.

FIG. 8 is a cross-sectional view of a multi-lumen catheter, according to yet another embodiment of the invention.

FIG. 9 is a cross-sectional view of a multi-lumen catheter, according to a still further embodiment of the invention.

DETAILED DESCRIPTION OF THE INVENTION, AND PREFERRED EMBODIMENTS THEREOF

The present invention relates to multi-lumen lay-flat tubing, catheters comprising such tubing, methods for making such tubing, and articles including such multi-lumen lay-flat tubing catheters.

In one aspect, the invention relates to a multi-lumen lay-flat tube formed of polymeric film material, comprising a main tube and at least one interior tubular passage, wherein each of the at least one interior tubular passage is constituted by reentrant portions of polymeric film material forming the main tube.

The polymeric film may comprise a thermoplastic elastomeric material, such as a polyurethane film material, or a laminate including barrier film, tie layers, and exterior layers.

In another aspect, the invention relates to a balloon catheter, comprising: a multi-lumen lay-flat tube formed of polymeric film material, comprising a main tube and at least one interior tubular passage, wherein each of the at least one interior tubular passage is constituted by reentrant portions of polymeric film material forming the main tube; and an inflatable balloon secured to one end of the main tube, with one of said at least one interior tubular passage being in fluid communication with an interior volume of the inflatable balloon.

The balloon catheter may be configured so that the one tubular passage is joined in fluid communication to a fluid feed tube, whereby an inflation fluid can be flowed through said fluid feed tube and said one tubular passage to said balloon for inflation thereof. The balloon catheter can further comprise a second interior tubular passage within said main tube, in which the second interior tubular passage terminating in an open end exterior of said balloon, whereby an irrigation fluid can be flowed through the second interior tubular passage to a local environment of said balloon.

The invention also contemplates a method of forming a multi-lumen lay-flat tube, comprising: providing superposed sheets of polymeric film material; welding the superposed sheets of polymeric film material along generally parallel, spaced-apart seam lines to form at least two passages bounded by a successive pair of said seam lines; and everting the welded superposed sheets to form a main tube having at least one tubular passage therewithin.

The features and aspects of the invention will be more fully apparent from the ensuing disclosure directed to the embodiments of FIGS. 1-6 hereof.

Figure 1:
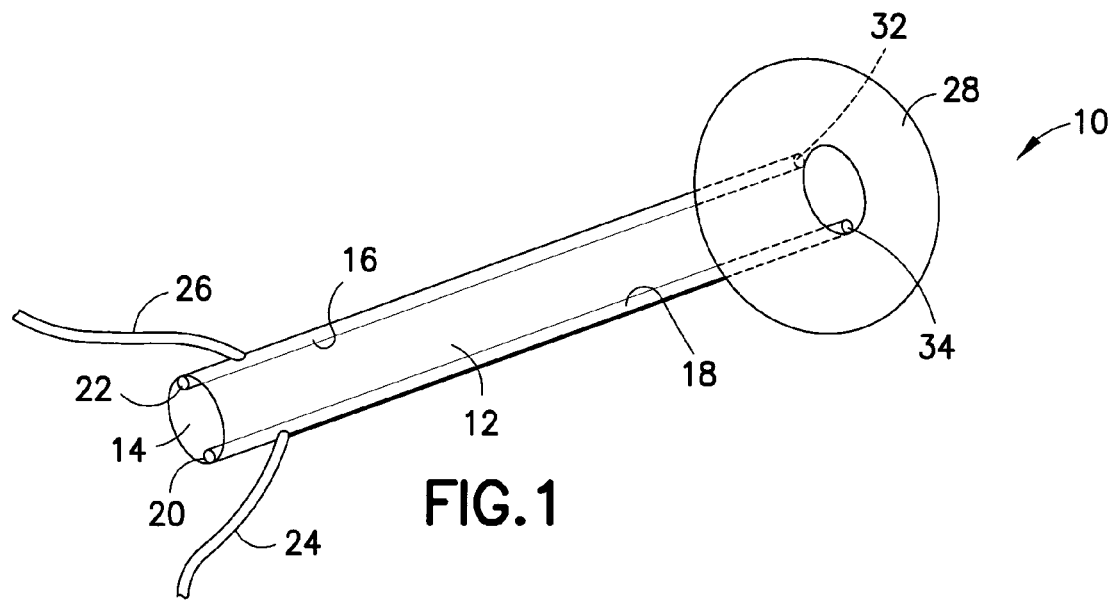
FIG. 1 is a perspective view of an indwelling balloon catheter, according to one embodiment of the present invention.

Referring now to the drawings, FIG. 1 is a perspective view of an indwelling balloon catheter 10, according to one embodiment of the present invention.

The indwelling balloon catheter 10 includes a main tubular body 12, of elongated conformation, defining an interior lumen 14 in which is disposed a first tubular passage member 16 and a second tubular passage member 18. The first tubular passage member 16 has an opening 22 at the proximal end of the device, and the second tubular passage member 18 as an opening 20 at the proximal end of the device, as illustrated. The first tubular passage member 16 has a gas feed tube 26 secured in fluid communication with the interior lumen of such member. In like manner, the second tubular passage member 18 has a fluid feed tube 24 secured in fluid communication with the interior lumen of the second tubular passage member.

At its proximal end, the main tubular body 12 is secured to an inflatable balloon 28. The first tubular passage member 16 has a distal end opening 32 in communication with the interior volume of the balloon. The second tubular passage member 18 has a distal end opening 34 that is open to the exterior environment of the balloon 28.

By the arrangement shown, the gas feed tube 26 can be coupled at its free proximal end with a source of pressurized gas, so that the pressurized gas flows through the gas feed tube 26 into the lumen of first tubular passage member 16, and passes into the interior volume of the balloon 28, for inflation thereof. The gas feed tube 26 may be coupled to a pressure shutoff valve, or a check valve that will seal and maintain balloon 28 in an inflated state.

The fluid feed tube 24 may be coupled to a source of irrigation fluid, such as water or other liquid, so that the irrigation fluid flows through the fluid feed tube 24 into the lumen of the second tubular passage member 18, and issues from the distal open end 34 of such second tubular passage member, to irrigate the local environment of the balloon 28. In such manner, the balloon catheter when positioned in the body of a human or other animal subject, with the balloon disposed in a body cavity or other physiological locus, is adapted to transmit irrigating fluid through fluid feed tube 24, second tubular passage member 18, and the open distal end 34 of such second tubular passage member, so that the physiological locus can be irrigated, and subsequently flow through the lumen of the main tubular body, for discharge at the proximal and thereof to a receptacle or other receiving means, such as a drain.

Figure 2:
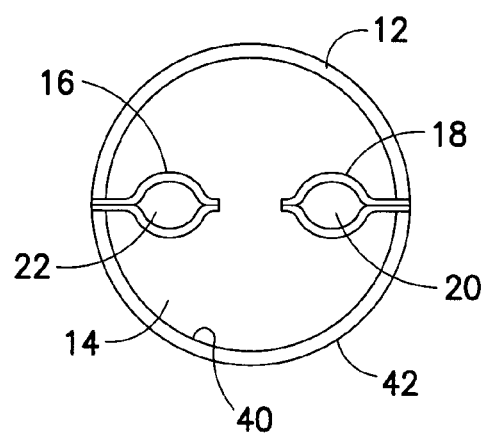
FIG. 2 is a cross-sectional view of the multi-lumen catheter of FIG. 1.

FIG. 2 is a cross-sectional view of the multi-lumen catheter of FIG. 1, at the main tubular body 12 thereof. The main tubular body 12 as shown defines an interior lumen 14, containing the first tubular passage member 16 defining lumen 22 therein and second tubular passage member 18 defining lumen 20 therein. The main tubular body 12 has an inner surface 40 bounding the lumen 14, and an exterior surface 42.

The invention in one aspect contemplates a method of catheterizing a human subject, comprising use of a balloon catheter of the type shown in FIG. 1, wherein the balloon is introduced into a body cavity of the human subject, and inflated by flow of gas through the interior tubular passage to the balloon.

Figure 3:
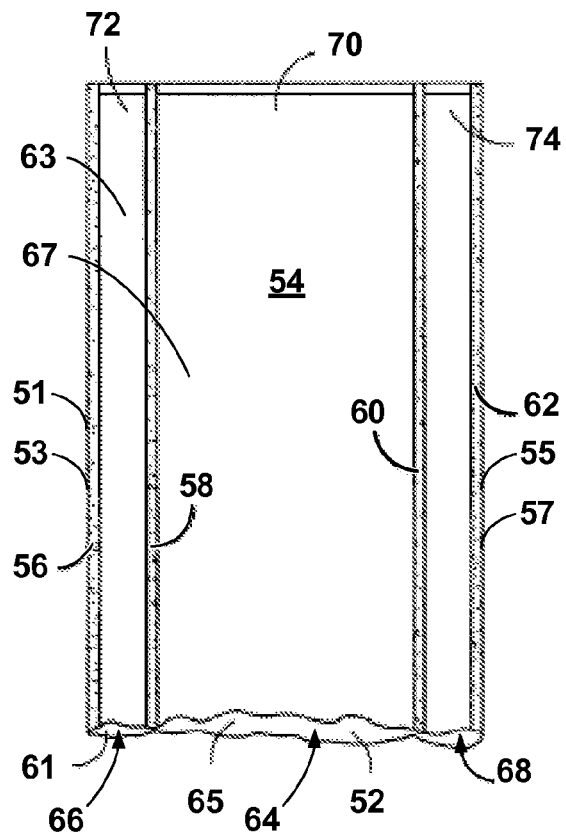
FIG. 3 is a view of two superposed sheets of polymeric material that have been welded at four seam lines.

FIG. 3 is a view of two superposed sheets 52, 54 of polymeric material that have been welded at four seam lines 56, 58, 60 and 62. A first sheet of polymeric material 52 has edges 51 and 55. A second sheet of polymeric edges has edges 53 and 57. Edges 51 and 55 are welded together by a first welded seam line 56. Edges 53 and 57 are welded together by a fourth welded seam line 62. By such welded seam lines, there is formed a central tube 70 bounding central tubular passage 64, first tubular passage member 72 bounding lumen 66, and second tubular passage member 74 bounding lumen 68. More specifically, as shown in FIG. 3, the first tubular passage member 72 is defined by the first welded seam line 56, a second welded seam line 58, a portion 61 of the first sheet of polymeric material 52 between the first welded seam line 56 and the second welded seam line 58, and a portion 63 of the second sheet of polymeric material 54 between the first welded seam line 56 and the second welded seam line 58. The central tubular passage 64 is defined by the second welded seam line 58, a third welded seam line 60, a portion 65 of the first sheet of polymeric material 52 between the second welded seam line 58 and the third welded seam line 60, and a portion 67 of the second sheet of polymeric material 54 between the second welded seam line 58 and the third welded seam line 60. In the embodiment of FIG. 3, a second tubular passage member 74 is defined by the third welded seam line 60, the fourth welded seam line joining the edges 55, 57 of the two sheets of polymeric material 52, 54, and portions of the two sheets of polymeric material 52, 54 between the third welded seam line 60 and the fourth welded seam line 62. The central tube 70 is configured to be everted, as described with reference to FIG. 4, so that the first tubular passage member 72 and the second tubular passage member are interiorly disposed within an additional lumen (not shown in FIG. 3) bounded by the everted central tube 70. Thus, the two sheets of polymeric material 52, 54 are joined only by the plurality of generally parallel welded seam lines 56, 58, 60, 62 joining edges of the two sheets of polymeric material 52, 54 or dividing the welded-together sheets of polymeric material 52, 54 into generally parallel tubular passage members.

The sheets 52, 54 of polymeric material may be of any suitable polymer construction, and may for example include polymeric materials such as polyethylene, polytetrafluoroethylene, polypropylene, polyurethane, polyvinylchloride, etc., with polyurethane in general being preferred. The twin sheets of polymeric material used in forming the multi-lumen tube of the invention may for example comprise a thermoplastic elastomer (TPE) material, and/or multilayer film, e.g., a laminate including barrier film, tie layers, and exterior layers. The two sheets that are welded to form the multi-lumen lay flat tube the invention may be the same as or different from one another.

The thickness of the sheets 52, 54 of polymeric material may be of any suitable dimension, and may for example have a thickness in a range of from about one mil up to 50 mils. The main tubular body may have any suitable inner and outer diameter dimensions. In various embodiments of the invention, the outer diameter is at least 0.25 inch, to accommodate the seam welding involved in the fabrication of the device.

The seam welding of the films may be carried out in any suitable manner, e.g., RF welding, impulse welding, ultrasonic welding, hotplate welding, hot wire welding, laser welding, etc. in general RF welding and laser welding are preferred techniques.

As illustrated in FIG. 3, the catheter article of the invention is formed as a lay-flat catheter article, i.e., such article is reposeable on a flat surface to assume a flat conformation.

Figure 4:
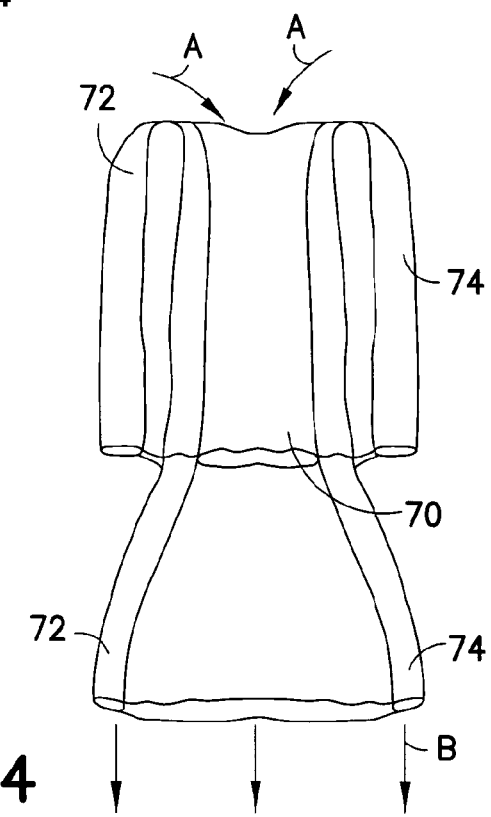
FIG. 4 is an elevational view of the welded sheet article of FIG. 3, during the eversion process.

FIG. 4 is an elevational view of the welded sheet article of FIG. 3, during the eversion process. All features and parts in FIG. 4 are numbered correspondingly with respect to the same features and parts in FIG. 3. As illustrated in FIG. 4, the lay-flat catheter article is everted (turned inside-out) so that the first and second tubular members 72 and 74, which were exterior to the central tube 70 in the as-formed state shown in FIG. 3, are in the everted state interiorly disposed in the central tube 70.

Figure 5:
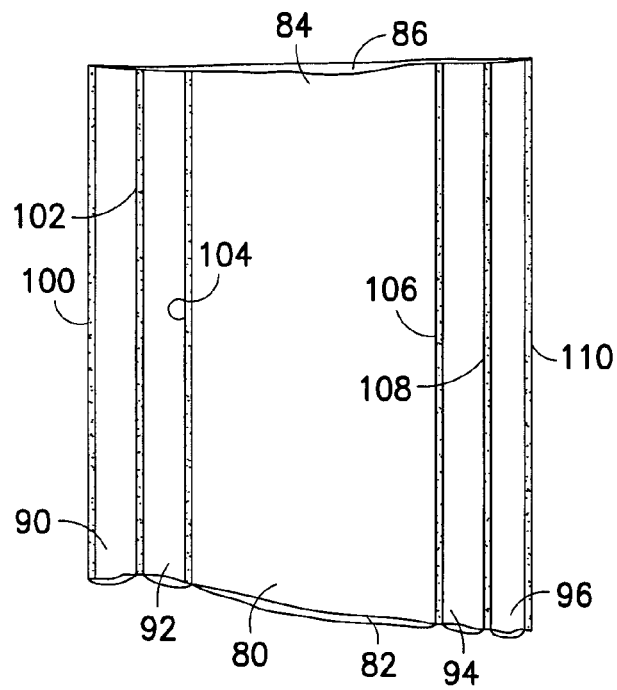
FIG. 5 is a view of two superposed sheets of polymeric material that have been welded at six seam lines.

FIG. 5 is a view of two superposed sheets 80, 82 of polymeric material that have been welded at six seam lines 100, 102, 104, 106, 108 and 110, thereby forming central tube 84 having interior lumen 86, first passage member 90, second passage member 92, third passage member 94 and fourth passage member 96.

Figure 6:
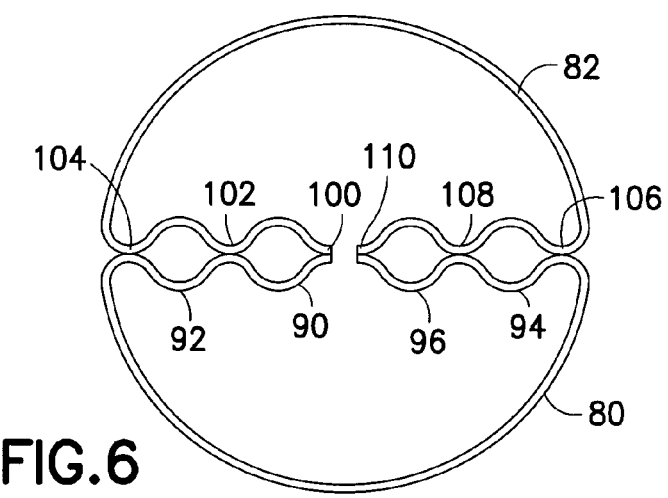
FIG. 6 is a cross-sectional view of the multi-lumen catheter of FIG. 5.

FIG. 6 is a cross-sectional view of a multi-lumen catheter formed by eversion of the welded sheet assembly of FIG. 5. All reference numerals in FIG. 6 correspond to those shown in FIG. 5. In the FIG. 6 catheter, four interior tubular passage members are provided.

It will be appreciated that any number of interior passages can be provided in the multi-lumen lay-flat catheter of the invention, as determined by the number of weld seam lines made at the margins of the superposed twin sheets of polymeric material. It will be apparent that the number of seam lines need not be the same at both sides of the superposed twin sheets, and that one side may for example provide two tubular passage members, while the other side may provide only one tubular passage member.

The invention therefore provides a multi-lumen lay-flat tube article useful for catheter applications, and as a component of catheter structures such as the balloon catheter device illustratively shown in FIG. 1 hereof.

The invention in another aspect provides a method of making a multi-lumen lay-flat tubing article, involving providing concentric first and second tube members, and heat sealing the first and second to members to one another at circumferentially spaced-apart locations extending lengthwise along the tube members, to form a passage bounded by the circumferentially spaced-apart heat seals and interior facing wall portions of the tube members between such heat seals.

A further aspect of the invention relates to a method of making a multi-lumen lay-flat tubing article, by providing concentric first and second tube members, and sealing the first and second to members to one another at circumferentially spaced-apart locations extending lengthwise along the tube members, to form a passage bounded by the circumferentially spaced-apart seals and interior facing wall portions of the tube members between such seals. Such method may further involve comprising the steps of providing a third tube member, and sealing the third tube member to the second tube member at circumferentially spaced-apart locations extending lengthwise along the second and third tube members, to thereby form at least one additional passage.

In another aspect, the invention contemplates a method of making a multi-lumen lay-flat tube, comprising the steps of providing a first tube member, and adhesively bonding margins of an elongate strip to a surface of the first tube member, to form a longitudinally extending passage bounded by facing surfaces of the elongate strip and first tube member and adhesively bonded margins of the elongate strip.

By methods such as those described above, multi-lumen lay-flat articles can be fabricated, e.g., a multi-lumen lay-flat tube, comprising concentric tube members, bonded to one another at longitudinally extending, circumferentially spaced-apart seals, to form at least one passage bounded by facing surfaces of the tube members and the circumferentially spaced-apart seals.

A further aspect of the invention relates to a multi-lumen lay-flat tube, comprising a tube member having bonded thereto a strip member longitudinally extending along the tube member, with the strip member bonded at margins thereof to the tube member to form an enclosed passage between the strip member and tube member. The bondant used for such purpose can be of any suitable type, e.g., a medical grade UV-curable adhesive composition.

FIG. 7 is a cross-sectional view of a multi-lumen catheter 120, according to another embodiment of the invention, constructed of concentric lay-flat tubing. The catheter 120 includes an inner concentric wall 142 and an outer concentric wall 140, defining an annular interior volume 130 therebetween. The inner concentric wall 142 bounds a central bore opening 146 of the catheter.

The annular interior volume 130 contains circumferentially spaced-apart seals, e.g., heat seals 122 and 124 defining an enclosed arcuate annular passage 132 bounded by the inner concentric wall 142, outer concentric wall 140, and heat seals 122 and 124. The seals instead of being heat seals may be adhesive seals, or other seal type.

In like manner, the annular interior volume 130 contains circumferentially spaced-apart seals, e.g., heat seals 126 and 128, defining an enclosed arcuate annular passage 130 bounded by the inner concentric wall 142, outer concentric wall 140, and heat seals 126 and 128.

By this arrangement, the respective arcuate annular passages 130 and 132 are formed, which may be utilized for delivery of fluids in the use of the catheter. For example, arcuate annular passage 130 may constitute an inflation passage for flow of an inflation gas to a balloon joined to one of the ends of the catheter, while the arcuate annular passage 132 may constitute an irrigation passage for flow of irrigating fluid along the catheter for delivery to an irrigation locus, e.g., a terminal opening delivering irrigation fluid into a body cavity, for irrigation of such cavity and efflux of the irrigation fluid from the body cavity through the central bore opening 146 of such catheter.

FIG. 8 is a cross-sectional view of a multi-lumen catheter 150 according to yet another embodiment of the invention. The catheter 150 includes three concentric lay-flat tubing elements, inner tube 156, intermediate tube 154 and outer tube 152, defining respective annular volumes 158 and 160, as illustrated.

The catheter features heat seals 168 and 164 between the inner and intermediate tubes, and heat seals 166 and 170 between the intermediate and outer tubes. This arrangement produces a multi-lumen lay-flat catheter having a central bore opening 162, two separated arcuate annular passages between the inner tube 156 and intermediate tube 154, bounded by the heat seals 164 and 168, and two separated arcuate annular passages between the intermediate tube 154 and outer tube 152, bounded by the heat seals 166 and 170.

FIG. 9 is a cross-sectional view of a multi-lumen catheter 180, according to a still further embodiment of the invention.

The catheter 180 in this embodiment features a main lay-flat tube 182, a first lay-flat exterior tube 184 enclosing interior volume 190, a second lay-flat exterior tube 186 enclosing interior volume 192, and heat seals 194, 196, 198 and 200. It will be appreciated that the catheter 180 of FIG. 9 can feature exterior tube passages, as illustrated, or the catheter article can be formed as shown in FIG. 9 and then everted, so that the formerly exterior tube passages become interior tube passages.

Figure 10:
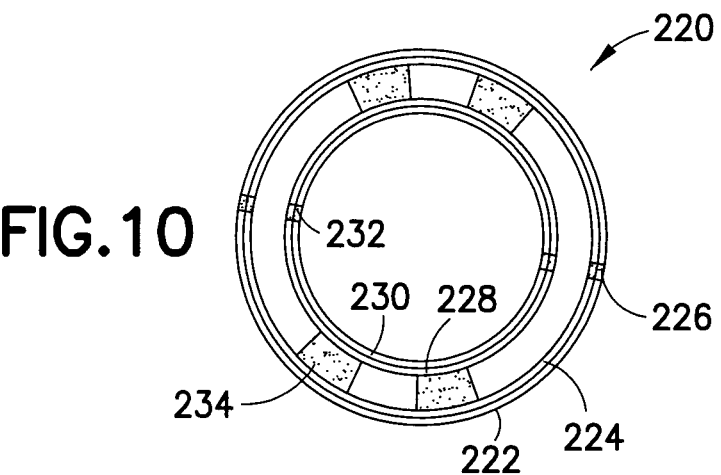
FIG. 10 is a cross-sectional view of a multi-lumen catheter, according to another embodiment of the invention.

FIG. 10 is a cross-sectional view of a multi-lumen catheter 220 according to another embodiment of the invention. The catheter 220 includes an inner concentric wall that is formed from two layers 228 and 230 of film that are bonded by heat seals 232 to one another to form the inner concentric wall. The outer concentric wall is likewise formed of two film material sheets 222 and 224 that are bonded together by heat seals 226. In this manner, each of the concentric inner and outer walls of the tube is formed of two sheets or strips of thin film material such as polyurethane, which are bonded at their margins to one another, to constitute a tubular body.

In this multi-lumen catheter 220, the inner and outer walls also are bonded to one another by heat seals 234. In lieu of heat seals, adhesive seals or other seal types could be used.

Figure 11:
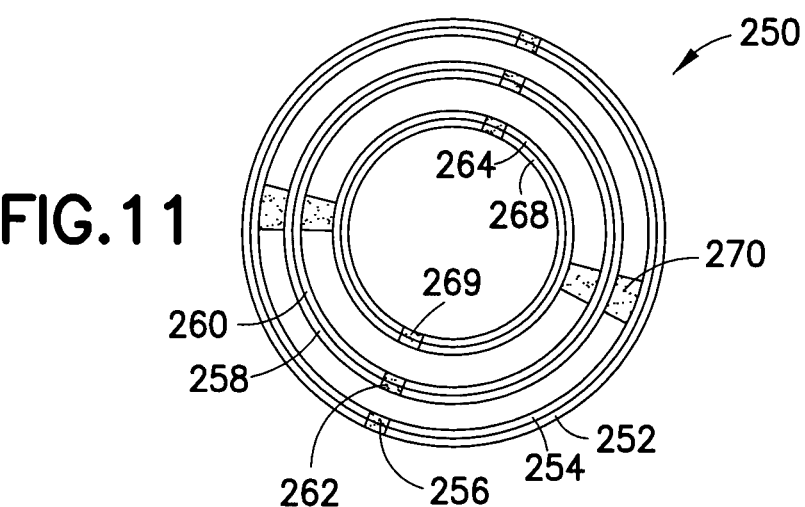
FIG. 11 is a cross-sectional view of a multi-lumen catheter, in another embodiment of the invention.

FIG. 11 is a cross-sectional view of a multi-lumen catheter 250 according to yet another embodiment of the invention. The catheter 250 includes three concentric tube elements, including an inner tube formed of two layers of film 264 and 268, bonded to one another by seal 269. An intermediate tube is formed from two layers of thin film 258 and 260, bonded to one another by seals 262. The outer concentric tube of the assembly is formed from respective sheets 252 and 254 of thin film material, bonded to one another by seals 256.

The inner, intermediate and outer tube elements of the assembly are bonded by heat seals 270 as shown, to form respective lumens in each of the annular volumes between successive tube elements of the assembly.

Figure 12:
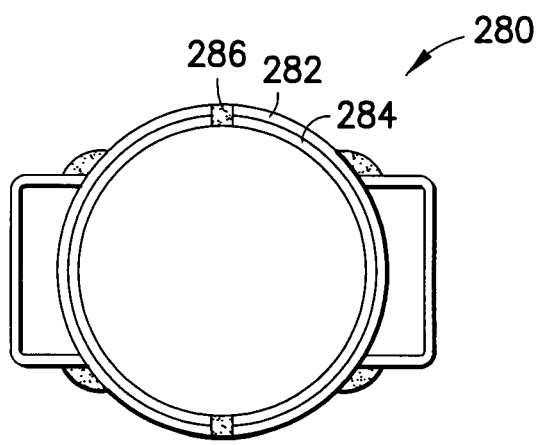
FIG. 12 is a cross-sectional view of a multi-lumen catheter, according to yet another embodiment of the invention.

FIG. 12 is a cross-sectional view of a multi-lumen catheter 280 according to a still further embodiment of the invention, having a conformation generally similar to that of FIG. 9. Whereas the tube 182 in the catheter of FIG. 9 is formed as a unitary main tube 182, the main tube of catheter 280 is formed from two layers 282, 284 that are bonded to one another by seals 286 at their respective margins, so that the bonded sheets constitute the main tubular element shown in FIG. 12.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A balloon catheter, comprising:
a multi-lumen lay-flat tube formed of:
a first sheet of polymeric film material having a first edge; and
a second sheet of polymeric film material having a first edge, the second sheet of polymeric film material being superimposed over and welded to the first sheet of polymeric film material by a first welded seam line joining the first edge of the first sheet of polymeric film material and the first edge of the second sheet of polymeric film material, a second welded seam line, and a third welded seam line, such that:
a first tubular passage member is defined by the first welded seam line, the second welded seam line, a first portion of the first sheet of polymeric film material between the first welded seam line and the second welded seam line, and a first portion of the second sheet of the polymeric film material between the first welded seam line and the second welded seam line, wherein the first tubular passage member bounds a first lumen; and
a central tube is defined by the second welded seam line, the third welded seam line, a second portion of the first sheet of polymeric film material between the second welded seam line and the third welded seam line, and a second portion of the second sheet of the polymeric film material between the second welded seam line and the third welded seam line, wherein the central tube is configured to be everted such that the first tubular passage member is interiorly disposed within the everted central tube; and an inflatable balloon secured to one end of the everted central tube, with said first lumen being in fluid communication with an interior volume of the inflatable balloon.

2. The balloon catheter of claim 1, wherein said polymeric film material comprises a thermoplastic elastomer material.

3. The balloon catheter of claim 1, wherein said polymeric film material comprises polyurethane film material.

4. The balloon catheter of claim 1, wherein said polymeric film material comprises a laminate including barrier film.

5. The balloon catheter of claim 1, wherein said polymeric film material has a thickness in a range of from 1 mil to 50 mils.

6. The balloon catheter of claim 1, wherein said tube has an outer diameter of at least 0.25 inch.

7. The balloon catheter of claim 1, wherein said at least three generally welded seam lines are formed by one of RF welding, impulse welding, ultrasonic welding, hotplate welding, hot wire welding, and laser welding.

8. The balloon catheter of claim 1, further comprising at least one additional interiorly disposed tubular passage member.

9. The balloon catheter of claim 1, wherein said first tubular passage member is joined in fluid communication to a fluid feed tube, whereby an inflation fluid can be flowed through said fluid feed tube and said first tubular passage member passage to said balloon for inflation thereof.

10. The balloon catheter of claim 9, further comprising a second tubular passage member within said central tube, said second tubular passage member terminating in an open end exterior of said balloon, whereby an irrigation fluid can be flowed through the second interiorly disposed longitudinally extending passage to a local environment of said balloon.

11. A method of catheterizing a human subject, comprising use of a balloon catheter as claimed in claim 1, wherein said balloon is introduced into a body cavity of said human subject, and inflated by flow of gas through said interior tubular passage to said balloon.

12. A multi-lumen lay-flat tube, comprising:
a first sheet of polymeric film material having a first edge; and
a second sheet of polymeric film material having a first edge, the second sheet of polymeric film material being superimposed over and welded to the first sheet of polymeric film material by a first welded seam line joining the first edge of the first sheet of polymeric film material and the first edge of the second sheet of polymeric film material, a second welded seam line, and a third welded seam line, such that:

a first tubular passage member is defined by the first welded seam line, the second welded seam line, a first portion of the first sheet of polymeric film material between the first welded seam line and the second welded seam line, and a first portion of the second sheet of the polymeric film material between the first welded seam line and the second welded seam line, wherein the first tubular passage member bounds a first lumen; and a central tube is defined by the second welded seam line, the third welded seam line, a second portion of the first sheet of polymeric film material between the second welded seam line and the third welded seam line, and a second portion of the second sheet of the polymeric film material between the second welded seam line and the third welded seam line, wherein the central tube is everted such that the first tubular passage member is interiorly disposed within an additional lumen bounded by the everted central tube.

13. An evertible multi-lumen lay flat tube, comprising two sheets of polymeric film material joined only by a plurality of generally parallel welded seam lines, wherein edges of the two sheets of polymeric film are joined to each other by two of the plurality of generally parallel welded seam lines and an additional welded seam line of the plurality of generally parallel welded seam lines joins the two sheets of polymeric material to each other between the joined edges of the two sheets of polymeric film to form two generally parallel tubular passage members, wherein a first of the two generally parallel tubular passage members is everted such that a second of the two generally parallel tubular passage members is internally disposed within the everted first of the two generally parallel tubes.

14. An evertible multi-lumen lay flat tube, comprising two sheets of polymeric film material joined only by a plurality of generally parallel welded seam lines, wherein edges of the two sheets of polymeric film are joined to each other by two of the plurality of generally parallel welded seam lines and an additional welded seam line of the plurality of generally parallel welded seam lines joins the two sheets of polymeric material to each other between the joined edges of the two sheets of polymeric film to form two generally parallel tubular passage members, wherein a first of the two generally parallel tubular passage members is evertible such that a second of the two generally parallel tubular passage members is internally disposed within the everted first of the two generally parallel tubes, further comprising an inflatable balloon secured to one end of the everted first of the two generally parallel tubular passage members and the second of two generally parallel tubular passage members being in fluid communication with an interior volume of the inflatable balloon.

* * * * *